United States Patent [19]
Day

[11] Patent Number: 5,084,764
[45] Date of Patent: Jan. 28, 1992

[54] PIPE INSPECTION SYSTEM
[75] Inventor: Robert C. L. Day, Bristol, United Kingdom
[73] Assignee: Northern Telecom Europe Limited, London, England
[21] Appl. No.: 673,678
[22] Filed: Mar. 22, 1991
[30] Foreign Application Priority Data
  Mar. 31, 1990 [GB] United Kingdom ............... 9007301
[51] Int. Cl.⁵ .............................................. H04N 7/18
[52] U.S. Cl. ................................ 358/100; 73/865.8
[58] Field of Search .............. 358/99, 100; 73/865.8; 354/63, 64; 15/104.061

[56] References Cited
U.S. PATENT DOCUMENTS

| | | | |
|---|---|---|---|
| 3,667,359 | 6/1972 | Walts et al. | 354/63 |
| 4,107,738 | 8/1978 | Van Norman | 358/100 |
| 4,372,658 | 2/1983 | O'Conner et al. | 354/63 |
| 4,651,558 | 3/1987 | Martin et al. | 368/100 |
| 4,848,168 | 7/1989 | Negishi | 73/865.8 |
| 4,953,412 | 9/1990 | Rosenberg et al. | 73/865.8 |

Primary Examiner—John K. Peng
Attorney, Agent, or Firm—Lee, Mann, Smith, McWilliams & Sweeney

[57] ABSTRACT

A method of inspecting a water pipeline while the pipeline is full of water comprises providing a liquid-tight casing housing a video camera and lights, coupled to a cable housing both optical and electrical conductors. A drogue is attached to the casing and the camera pod and drogue are launched through the sidewall of the pipeline via a launch chamber. The camera pod and cable are neutrally buoyant and can be deployed several kilometers along the pipeline for inspecting the pipeline and recovered again into the launch chamber. The advantage of this system over conventional systems is that much longer lengths of pipeline can be inspected from a single location.

9 Claims, 4 Drawing Sheets

PIPE INSPECTION SYSTEM

This invention relates to inspecting pipes internally, particularly but not exclusively water pipes.

BACKGROUND OF THE INVENTION

A known system for inspecting pipes comprises a T.V. camera mounted on a sled which is pushed by a semi-rigid cable along the pipe from an open end of the pipe. The arrangement has lights to illuminate the interior of the pipe, and the light and the camera are powered via the cable.

A limitation of this system is the relatively short distance the camera can be pushed into the pipe e.g. 300 meters maximum. Another problem resides in the fact that only dry pipes can be inspected although provided the entrance is dry the camera can tolerate flooded regions of pipes in downhill portions of the pipeline.

It is an object of the present invention to provided an improved inspection system which can overcome the problems outlined above.

SUMMARY OF THE INVENTION

According to the present invention there is provided a pipeline inspection system comprising a liquid pressure tight casing incorporating a video camera for viewing the inside of the pipeline and lights for illuminating the inside of the pipeline, a cable for carrying power to the camera and the lights and for carrying the video signal from the camera, and a drogue for attachment to the casing and/or the cable, the system being substantially neutrally buoyant in liquid flowing in the pipeline and the drogue acting to provide a pulling force on the cable by reaction against the liquid flowing in the pipeline.

In a preferred embodiment of the invention the camera and cable are inserted through the side wall of the pipeline via an inclined entrance pipe having an outer gland which fits around the cable, a chamber for housing the camera and drogue and a valve for closing the chamber off from the pipeline.

According to another aspect there is provided a method of inspecting a pipeline comprising providing a liquid tight casing incorporating a video camera and lights, a cable coupled to the casing for carrying power to the camera and the lights and for carrying the video signal from the camera, and a drogue attached to the casing and/or the cable, the method comprising launching the camera and drogue into the pipeline while the pipeline contains flowing liquid, and controlling the deployment of the cable from the location of launch, the cable and the casing being substantially neutrally buoyant in the liquid, and inspecting the inside of the pipeline by means of the video signal transmitted by the camera back to the launch location.

BRIEF DESCRIPTION OF THE DRAWINGS

In order that the invention can be clearly understood, reference will now be made to the accompanying drawings, in which.

DESCRIPTION OF PREFERRED EMBODIMENT

Figure 1:
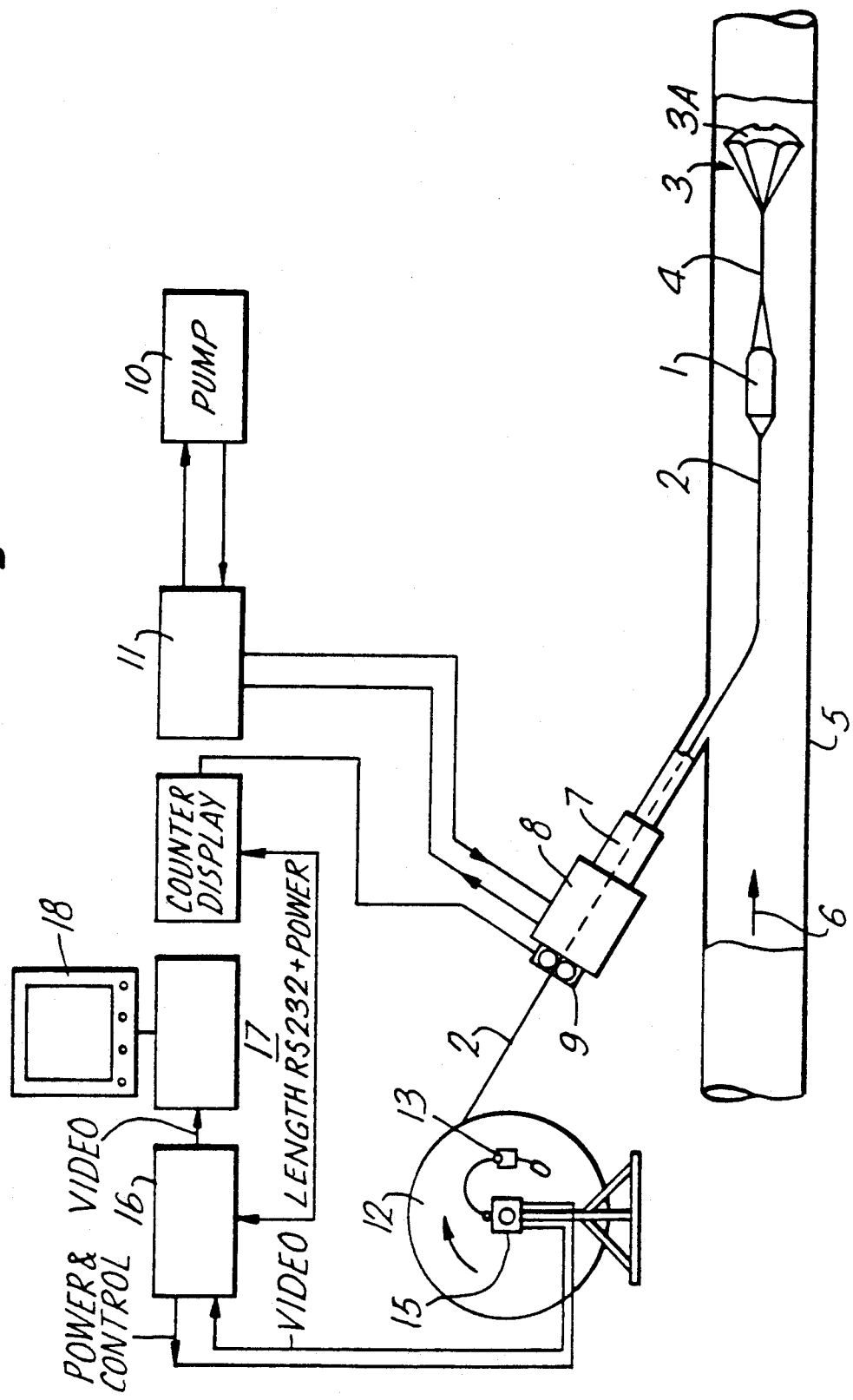
FIG. 1 shows diagrammatically an inspection system being deployed, according to an embodiment of the invention.

Referring to the drawings the system comprises a camera pod 1 which is waterproof and has a pressure rating of over 100 psi (250 psi in this embodiment) and which at its rear end is connected to a cable 2 incorporating electrical and optical conductors and can be constructed according to the teachings of our GB patent 2122367B.

The pod 1 is coupled to a drogue 3 by a line 4. The drogue has a central aperture 3A.

Figure 2:
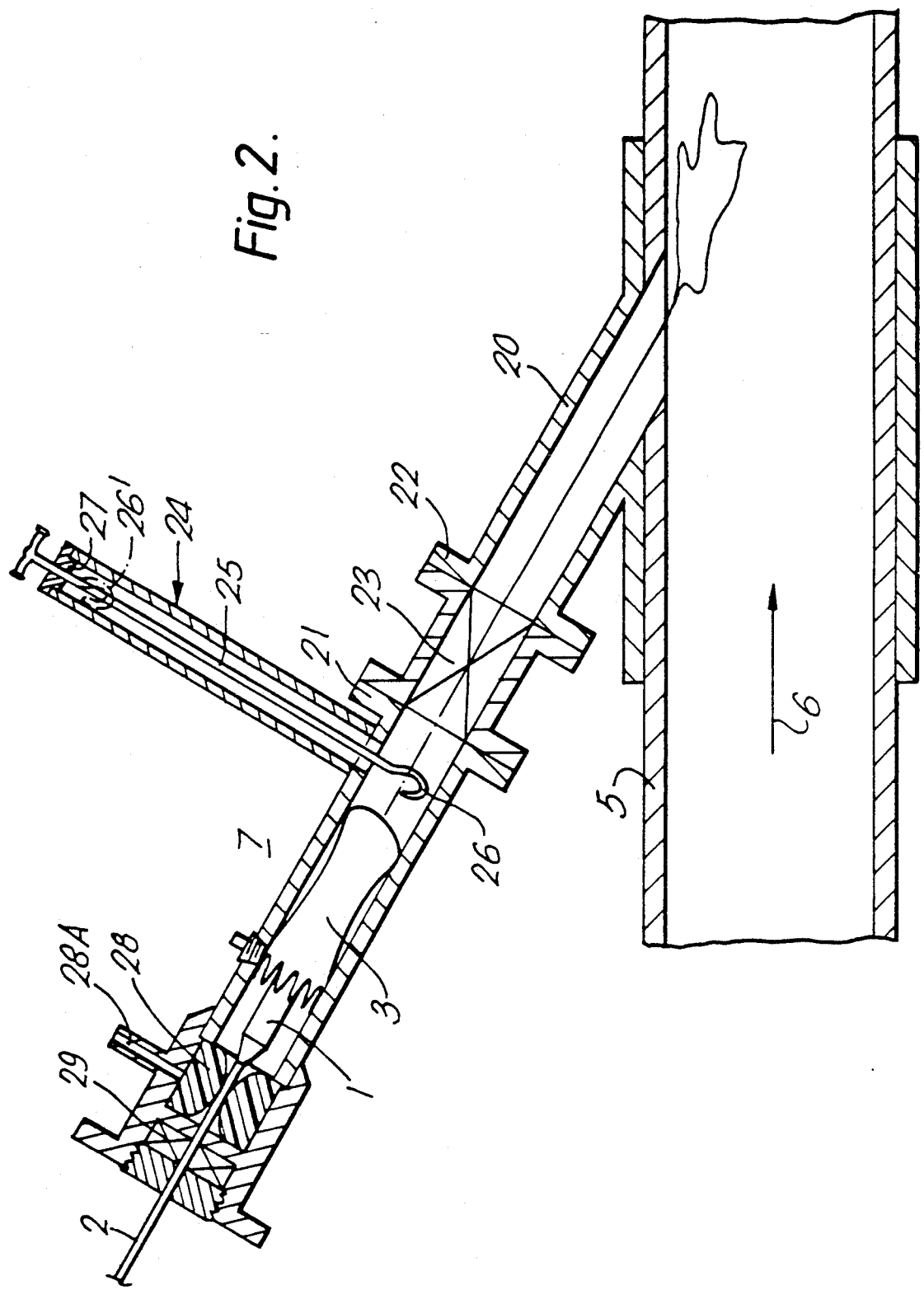
FIG. 2 shows in greater detail the launch chamber of FIG. 1.

The camera pod, drogue and cable are shown being deployed in an underground water pipeline 5, through which water is flowing in the direction of the arrow 6, via a sidewall entry chamber 7 shown in greater detail in FIG. 2 where the pod and drogue are stored in preparation for deployment.

Behind the launch chamber 7 is a cable drive unit 8 and a cable length counter 9. The drive unit is powered hydraulically from a pump 10 via drive control unit 11.

The cable 2 is wound on a drum 12 and its end connected to an opto-electronic convertor 13 which for the optical video signal from the camera, converts it to an electrical signal, and this together with the power feed is coupled through a slip ring arrangement 15 to the counter and video inspection unit 16 which feeds the video signal to the video recorder 17 and displays the view from the camera pod on the monitor 18.

The counter display unit displays the length of cable deployed and deployment velocity from the signal from 9 and is coupled to the control and video insertion unit 16.

Referring now to FIG. 2 the launch chamber 7 houses the camera pod 1 and the drogue 3 and is removably secured to a hot tap saddle 20 by a mounting flange 21 on the chamber 7, a flange 22 on the hot tap saddle 20, and an individual gate valve 23 with flanges. The valve 23 is operable to open and close the hot tap saddle 20.

The launch chamber 7 incorporates an hydraulically activated cable seal 28 directly below a primary dynamic cable seal 29. This hydraulic device is activated by hydraulic pressure applied via the port 28A but would only be activated if there were a need to change the primary seals during a deployment. Both seals are easily removed from the chamber for maintenance etc.

Mounted on the chamber 7 is a hollow tubular drogue storage device 24 for storing the drogue after the camera pod has been withdrawn back into the chamber 7. The drogue is drawn back through the valve so the valve can be closed after inspection has been completed. The storage device 24 comprises a recovery rod 25 with a grab 26 at the end, the rod being slideable in an end seal 27 to pull the drogue up inside the storage device, the upper position 26' of the grab 26 being represented in broken line.

Figure 3:
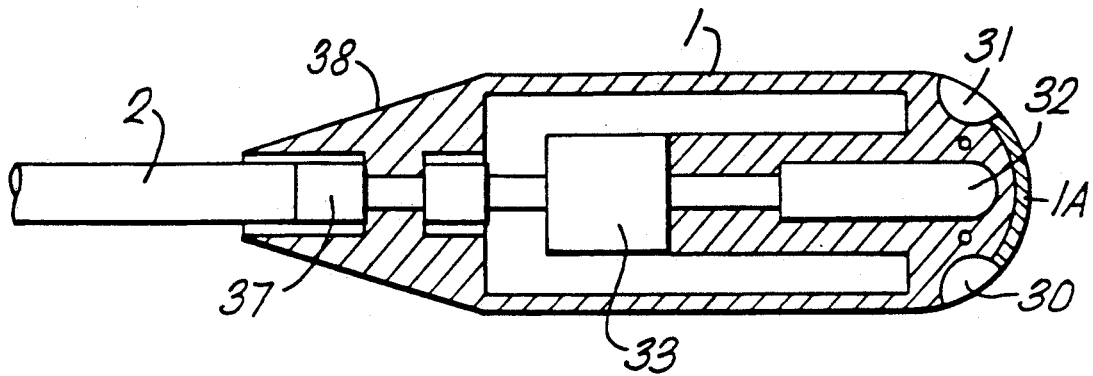
FIG. 3 shows diagrammatically the camera pod and FIG. 3A the circuitry of FIG. 1.
Figure 3A:
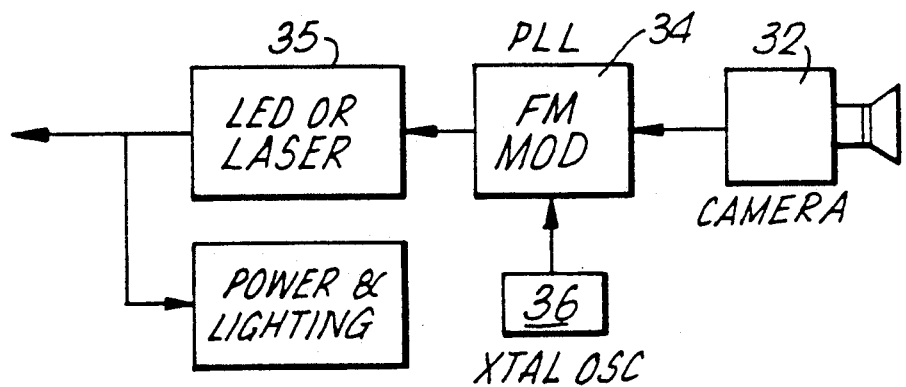

Referring to FIG. 3 the camera pod 1 is pressure resistant and houses electric lights 30, 31 a camera 32 such as one manufactured by Pulnix, and an electro-optical interface unit 33. This includes an FM modulation 34 to modulate the camera output signal for controlling an LED or laser 35 at a frequency determined by a local crystal oscillator 36, as shown in block schematic form in FIG. 3A. This optical signal is coupled into an optical fibre of the cable via a cable strain termination 37 which is preferably field-rateable. A bend restrictor 38 is secured to the rear of the pod 1 and is of stiff rubber. It embraces the cable end and the termination and limits the band radius of the cable adjacent the pod to protect the cable from damage. The fibre is multimode in this embodiment, but could be single mode. The pod may be split into two or three pod sections with flexible links.

The video transmit and receive electronics system is one sold by STC Video Systems of Cwmbran, Gwent. In operation the camera pod and drogue are pushed into the pipeline until the drogue inflates as shown diagrammatically in FIG. 1.

The lights in the pod illuminate the interior of the pipeline 5. The cable and the pod are neutrally buoyant in the water and the flowing water produces a drag on the drogue which maintains the camera pod substantially central in the pipeline.

The camera views the interior of the pipeline through a transparent window 1A and can also see through the aperture 3A in the drogue. The images formed by the camera are transmitted to the monitor 18 and recorded on the recorder 17 via an optical fibre in the cable. Power conductors in the cable power the lights, the opto electronics and the camera in the camera pod. The cable drive device 8 under the control of the drive control 11 feeds the cable and camera into the pipeline for lengths up to say five kilometers. The pull on the drogue and the drag of the liquid on the cable enable very long lengths of pipeline to be inspected downstream of the launch location, and the drive device 8 is mostly used to brake the cable against the drag of the liquid and of course to recover the cable back through the launch chamber after each deployment.

Figure 4A:
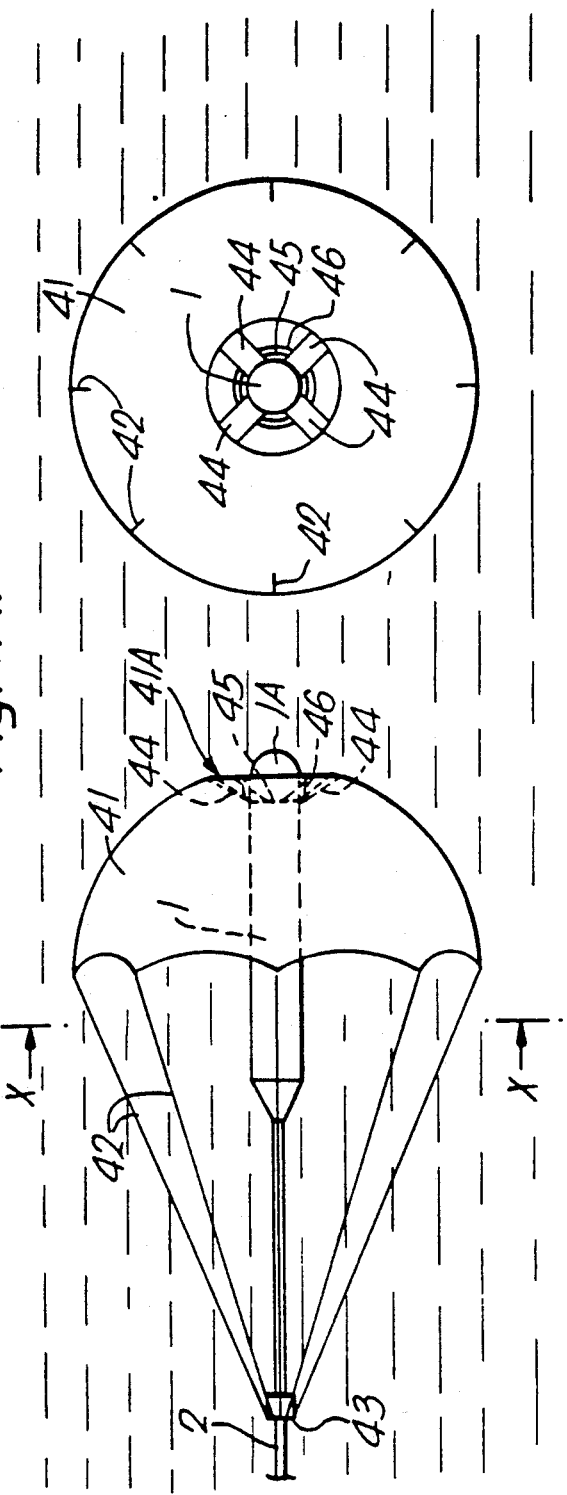
FIGS. 4A and 4B show respective alternative drogue arrangements.
Figure 4B:
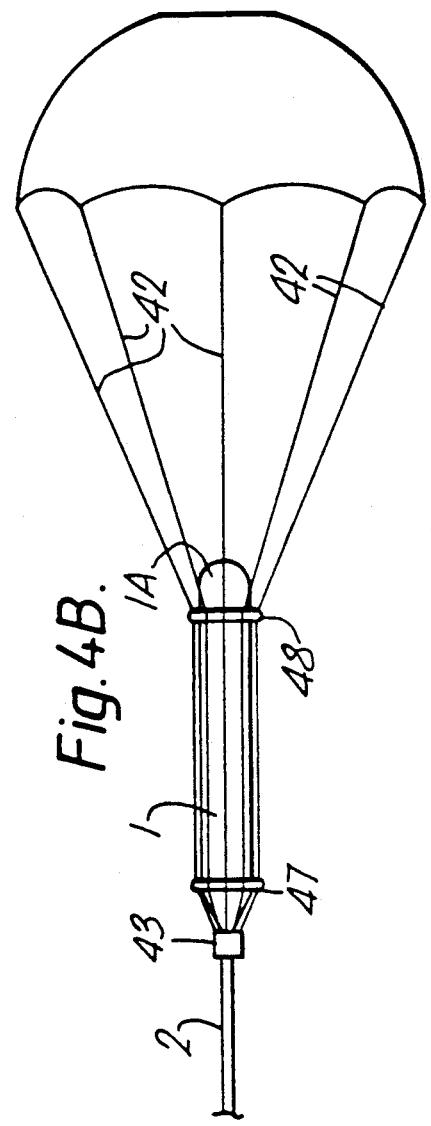

Referring now to FIG. 4 there are shown two drogue arrangements alternative to the one depicted in FIG. 1. Firstly FIG. 4A shows a drogue 41 with the camera lens 1A located at the drogue apex 41A so that the camera can see forward and sidward without constraint. The drogue rigging lines 42 are anchored to a cable clamp fixing 43 and the drogue has several (four in this embodiment) anchor tapes 44 anchored to a cord 45 tied behind a step 46 near the front end of the camera pod 1.

FIG. 4B once again shows the drogue rigging lines 42 anchored to the cable 2 by a cable clamp fixing 43 but here the lines 42 are longer and pass through rigging line separators 47 and 48 secured to the camera pod 1, so that the camera has at the drogue rigging line confluence.

Figure 5:
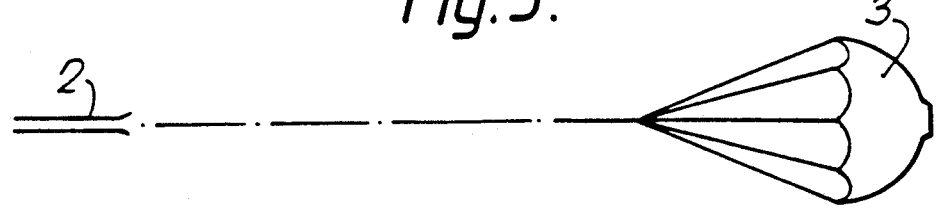
FIG. 5 shows a further modification.

The camera pod 1 can be split into separate sections as shown in FIG. 5, and this arrangement is suitable for small-diameter pipe inspection. FIG. 5 shows schematically an electro-optic section 51 coupled by a flexible link 52 a camera section 53 with lights. The drogue 3 is similar to the drogue shown in FIG. 1 and directly coupled to the casing 53, but the alternative versions shown in FIG. 4 could also be employed here.

In some applications the pod may be provided with a neutrally buoyant sonde unit to enable transmission of a signal whereby the precise position of the pod may be determined by suitable detection equipment on the exterior of the pipe line. It will be appreciated that, even though the cable length is known accurately, small map errors or unrecorded bends in the pipe route can result in significant pipe length errors, e.g. a few meters, over distances of two to three kilometers.

A hydrophone may be fitted to the rear end of the pod whereby to transmit acoustic information back down the optical fibre. This information can be processed to identify small leaks which may not be apparent from visual inspection.

I claim:

1. A pipeline inspection system comprising a liquid pressure tight casing incorporating a video camera for viewing the inside of the pipeline and lights for illuminating the inside of the pipeline, a cable for carrying power to the camera and the lights and for carrying the video signal from the camera, and a drogue for attachment the cable, the system being substantially neutrally buoyant in liquid flowing in the pipeline and the drogue acting to provide a pulling force on the cable by reaction against the liquid flowing in the pipeline.

2. A system as claimed in claim 1, comprising a launching chamber for launching the system at an angle through the sidewall of the pipeline, a valve for closing the chamber, and means for recovering the drogue from the pipeline to a position behind the valve after the casing has returned to the chamber.

3. A system as claimed in claim 2 comprising a cable drive mechanism to drive the cable into the pipeline and to recover the cable from the pipeline, and to provide a brake during inspection of the pipeline.

4. A system as claimed in claim 1, wherein the cable incorporates an optical fibre for the video signal transmission.

5. A system as claimed in claim 1, wherein the drogue has rigging lines anchored to the cable at a location close to the casing.

6. A system as claimed in claim 5, wherein the casing projects into the apex of the drogue, the drogue having an aperture at its apex, and the casing is coupled to the drogue apex.

7. A system as claimed in claim 1, wherein the drogue is attached to the cable via the casing.

8. A method of inspecting a pipeline comprising providing a liquid tight casing incorporating a video camera and lights, a cable coupled to the casing for carrying power to the camera and the lights and for carrying the video signal from the camera, and a drogue attached to the cable, the method comprising launching the camera and drogue into the pipeline while the pipeline contains flowing liquid, and controlling the deployment of the cable from the location of launch, the cable and the casing being substantially neutrally buoyant in the liquid, and inspecting the inside of the pipeline by means of the video signal transmitted by the camera back to the launch location.

9. A method as claimed in claim 8, wherein the drogue is attached to the cable via the casing.

* * * * *